US00PP08940P

United States Patent [19]

Zary

[11] Patent Number: Plant 8,940

[45] Date of Patent: Oct. 18, 1994

[54] MINIATURE ROSE PLANT NAMED JACPLY

[75] Inventor: Keith W. Zary, Thousand Oaks, Calif.

[73] Assignee: Bear Creek Gardens, Inc., Medford, Oreg.

[21] Appl. No.: 150,390

[22] Filed: Nov. 9, 1993

[51] Int. Cl.[5] ..... A01H 5/00

[52] U.S. Cl. ..... Plt./7.1

[58] Field of Search ..... Plt. 7.1, 8.2, 22

*Primary Examiner*—Howard J. Locker

*Attorney, Agent, or Firm*—Klarquist Sparkman Campbell Leigh & Whinston

[57] ABSTRACT

Miniature rose plant having high-centered flowers of changing orange, yellow and pink; disease-resistant, dark green and glossy foliage; and vigorous, upright, well-branched growth.

1 Drawing Sheet

The present invention relates to a new and distinct variety of rose plant of the miniature class that was originated by me by crossing two unnamed seedlings.

The primary objective of this breeding was to produce a new rose variety having the dark green, glossy foliage and vigor of the orange-flowered female seedling combined with the high petal count, high-centered form and yellow color of the male parent. The objective was substantially achieved, along with other desirable improvements, as evidenced by the following unique combination of characteristics that are outstanding in the new variety and that distinguish it from its parents, as well as from all other varieties of which I am aware:

1. A vigorous, upright, well-branched growth habit;
2. Bright orange, yellow and pink flowers;
3. Good high-centered flower form;
4. Dark green, glossy, healthy foliage; and
5. Resistance to powdery mildew and rose rust.

Asexual reproduction of this new variety by softwood cuttings as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—Unnamed seedling.

*Pollen parent.*—Unnamed seedling.

Classification:

*Botanical.*—*Rosa hybrida.*

*Commercial.*—Miniature.

FLOWER

Observations made from specimens grown in a garden environment in Somis, Calif., from March through July, 1993.

Blooming habit: Continuous.

Bud:

*Size.*—½ inch long when the petals start to unfurl.

*Form.*—Long, pointed ovoid.

*Color.*—When sepals first divide, bud color is Orange-Red Group 34A. When half blown, the upper sides of the petals are Orange-Red Group 30D in the flower center, Red Group 52C to D on the petals on the edge of the flower; and the lower sides of the petals are a mixture of colors between Orange-Red Group 34A and Yellow-Orange Group 15C.

*Sepals.*—Color: Green Group 138B. Surface texture: Covered in fine hairs. There are three normally appendaged sepals. There are two unappendaged sepals with hairy edges.

*Receptacle.*—Color: Green Group 137B. Shape: Funnel. Size: Small (⅛ inch×⅛ inch). Surface: Smooth.

*Peduncle.*—Length: Short (1¼ inch×1½ inch). Surface: Smooth with a few glands. Color: Medium green and bronzy. Strength: Stiff, erect.

Bloom:

*Size.*—Small. Average open size is 1½ inches in diameter.

*Borne.*—Several together in pyramidal clusters of 5 to 15 flowers.

*Stems.*—Short (6 to 8 inches) and strong.

*Form.*—When first open: High centered. Permanence: Flattens.

*Petalage.*—Number of petals under normal conditions: 25 to 30.

*Color.*—The upper side of the petals begin as Orange-Red Group 30D, changing to Red Group 52C-D when half open, to Yellow-Orange Group 15C when fully open and to Red Group 41C when near cleaning. The reverse side of the petals is a mixture of colors between Orange-Red Group 34A and Yellow-Orange Group 15C. The base of each petal has a distinct Yellow-Orange Group 15C half moon at the point of attachment. The major color on the upper side is Yellow-Orange Group 15C.

*Variegations.*—None.

*Discoloration.*—The general tonality at the end of the first day: Little change. At the end of the third day, gradual shift from Orange-Red Group 30D to Red Group 52C-D on petal edges to Yellow-Orange Group 15C when fully open and finishing mostly with Red Group 41C.

*Fragrance.*—Slight.

Petals:

*Texture.*—Thick.

*Shape.*—Oval.

*Form.*—Tips are slightly recurved and edges slightly quilled.

*Arrangement.*—Imbricated, with few petaloids in the center.

*Persistence.*—Drop off cleanly.

*Lastingness.*—On the plant: Fair (5 to 6 days). As a cut flower: Fair (5 to 6 days).

Reproductive parts:

*Anthers.*—Size: Medium. Quantity: Many. Color: Yellow. Arrangement: Regular around the styles, mixed with occasional petaloids.

*Filaments.*—Color: Yellow.

*Pollen.*—Color: Gold-yellow.

*Styles.*—Color: Red.

*Stigmas.*—Color: Greenish-white.

Form: Bush.

Growth: Vigorous, dwarf, upright, branching. Height at maturity is 24 inches, width is 18 inches.

Foliage:

*Number of leaflets on normal mid-stem leaves.*—5 or 7.

*Size.*—Small ($2\frac{1}{2}$ inches$\times 1\frac{1}{2}$ inches).

*Quantity.*—Normal.

*Color.*—New foliage: Bronze. Old foliage: Glossy, Green Group 139A.

Leaflets:

*Shape.*—Pointed oval.

*Texture.*—Upper side: Leathery, glossy.

*Edge.*—Serrated.

*Serration.*—Single and small.

*Petiole rachis.*—Color: Reddish becoming green.

*Petiole underside.*—Smooth with occasional prickles.

*Stipules.*—Short and bearded.

*Disease resistance.*—Resistant to mildew and rust under normal growing conditions at Somis, Calif.

Wood:

*New wood.*—Color: Reddish. Bark: Smooth.

*Old wood.*—Color: Green. Bark: Smooth.

Prickles:

*Quantity.*—Ordinary on main canes from base. Ordinary on laterals from main canes.

*Form.*—Short ($\frac{1}{8}$ inch), hooked slightly downward.

*Color when young.*—Red.

Small prickles:

*Quantity.*—None on main stalks. None on laterals.

I claim:

1. A new and distinct variety of rose plant of the miniature class, substantially as herein shown and described, characterized particularly as to novelty by the unique combination of its attractive but changing orange, yellow and pink flower colors; its disease-resistant, dark green and glossy foliage; its vigorous, upright, well-branched growth; and its attractive, high-centered flowers.

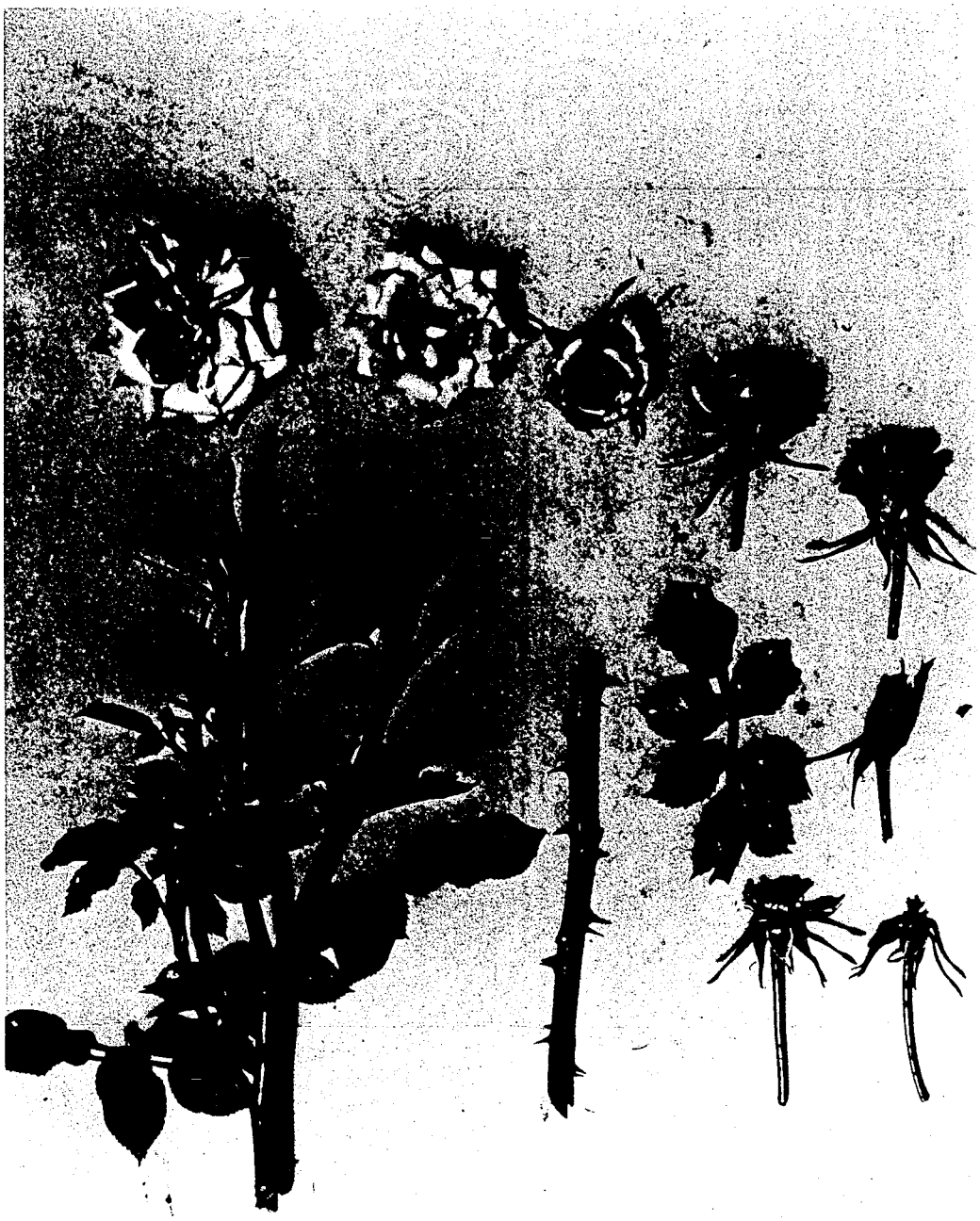

* * * * *